United States Patent
Itsuji

(10) Patent No.: US 8,405,406 B2
(45) Date of Patent: Mar. 26, 2013

(54) DETECTING APPARATUS AND IMAGING APPARATUS

(75) Inventor: Takeaki Itsuji, Hiratsuka (JP)

(73) Assignee: Canon Kabushiki Kaisha, Tokyo (JP)

( * ) Notice: Subject to any disclaimer, the term of this patent is extended or adjusted under 35 U.S.C. 154(b) by 1002 days.

(21) Appl. No.: 12/281,639

(22) PCT Filed: Mar. 27, 2008

(86) PCT No.: PCT/JP2008/056616
§ 371 (c)(1),
(2), (4) Date: Sep. 4, 2008

(87) PCT Pub. No.: WO2008/123555
PCT Pub. Date: Oct. 16, 2008

(65) Prior Publication Data
US 2011/0241699 A1  Oct. 6, 2011

(30) Foreign Application Priority Data
Mar. 30, 2007 (JP) .................................. 2007-092831

(51) Int. Cl.
*G01R 27/04* (2006.01)
(52) U.S. Cl. ........ 324/639; 356/495; 356/450; 356/451; 356/456; 250/330; 250/338.1; 250/358.1; 250/341.1; 324/71.5; 324/96
(58) Field of Classification Search .............. 356/51, 356/450, 451, 456; 250/330, 338.1, 341.1, 250/358.1, 339.02, 339.06, 339.07; 324/71.5, 324/96, 639
See application file for complete search history.

(56) References Cited

U.S. PATENT DOCUMENTS

| | | | |
|---|---|---|---|
| 5,710,430 A | 1/1998 | Nuss | 250/358.1 |
| 6,061,133 A | 5/2000 | Freischlad | 356/460 |

(Continued)

FOREIGN PATENT DOCUMENTS

| | | |
|---|---|---|
| EP | 1 526 355 A1 | 4/2005 |
| EP | 1643236 | 4/2006 |

(Continued)

OTHER PUBLICATIONS

Office Action dated Sep. 27, 2011, issued in counterpart Japanese Application No. 2007-092831, and translation.

(Continued)

*Primary Examiner* — Jermele M Hollington
*Assistant Examiner* — Son Le
(74) *Attorney, Agent, or Firm* — Fitzpatrick, Cella, Harper & Scinto

(57) ABSTRACT

A detection apparatus and an imaging apparatus are capable of accurately conducting non-destructive observation of a target by using an incoherent electromagnetic wave. The detection apparatus has a generating section, a first coupler section, a delaying section, a second coupler section and a signal processing section. The generating section 101 includes a coherent electromagnetic wave source 102 and a diffusing section 103 for generating a pseudoincoherent electromagnetic wave by changing a propagation state of the coherent electromagnetic wave in accordance with a code pattern. The incoherent electromagnetic wave is split into first and second waves and the first wave is affected by the target of observation while the second wave is delayed by the delaying section. The first and second waves are then coupled to produce a coupled wave having a correlation signal of them and the signal is utilized to acquire information on the inside of the target of observation.

10 Claims, 6 Drawing Sheets

U.S. PATENT DOCUMENTS

| | | | |
|---|---|---|---|
| 6,088,100 A * | 7/2000 | Brenan et al. | 356/456 |
| 7,486,402 B2 * | 2/2009 | Chan et al. | 356/495 |
| 2003/0055342 A1 | 3/2003 | Toida et al. | 600/478 |
| 2003/0178584 A1 | 9/2003 | Arnone et al. | 250/495.1 |
| 2007/0052953 A1 * | 3/2007 | Hill | 356/237.2 |
| 2007/0215810 A1 | 9/2007 | Kurosaka et al. | 250/358.1 |
| 2007/0252992 A1 | 11/2007 | Itsuji | 356/369 |
| 2007/0273357 A1 * | 11/2007 | Saito et al. | 324/71.5 |
| 2007/0279136 A1 | 12/2007 | Koyama et al. | 331/107 T |
| 2007/0279143 A1 | 12/2007 | Itsuji | 331/185 |
| 2008/0048678 A1 | 2/2008 | Kurosaka et al. | 324/639 |
| 2008/0116374 A1 | 5/2008 | Ouchi et al. | 250/306 |
| 2008/0210873 A1 | 9/2008 | Itsuji | 250/347 |
| 2009/0059205 A1 | 3/2009 | Itsuji | 356/51 |

FOREIGN PATENT DOCUMENTS

| | | |
|---|---|---|
| GB | 2 359 716 A | 8/2001 |
| JP | 4-174345 | 6/1992 |
| JP | 10-90174 | 4/1998 |
| JP | 2003-090972 | 3/2003 |

OTHER PUBLICATIONS

Extended European Search Report issued May 10, 2012, in counterpart European Patent Application No. 12150874.1.

* cited by examiner

DETECTING APPARATUS AND IMAGING APPARATUS

This application is a national stage filing under 35 U.S.C. §371 of International Application No. PCT/JP2008/056616, filed Mar. 27, 2008.

TECHNICAL FIELD

The present invention relates to a detection apparatus for acquiring information on a target of observation by means of an electromagnetic wave and also to an imaging apparatus for acquiring an image of a target of observation.

BACKGROUND ART

Non-destructive testing techniques have been developed in recent years, using high frequency electromagnetic waves including frequencies of an arbitrarily selected frequency band (to be referred to as terahertz waves hereinafter) out of from the millimeter wave to the terahertz wave region (from 30 GHz down to 30 THz). Terahertz waves are known to contain absorption lines of various different substances including those of biomolecules. Applications of the frequency range include safe imaging techniques for fluoroscopic examinations that can eliminate the use of X-rays and spectrometric techniques for looking into the bonding conditions of molecules by determining the absorption spectra and the complex permittivity values inside various substances. Further, techniques for analyzing biomolecules as well as techniques for estimating concentration and mobilities of carriers are expected.

Non-destructive examination techniques and imaging techniques using pulse signals in the order of picoseconds (or terahertz waves) have been proposed (see, inter alia, Japanese Patent Application Laid-Open No. H10-090174). These techniques relate to two-dimensional imaging. Imaging techniques for detecting scattered light from the boundary of adjacent layers showing different refractive indexes and acquiring information in the depth direction by using an incoherent electromagnetic wave source have also been proposed (see, inter alia, Japanese Patent Publication No. H06-035946).

DISCLOSURE OF THE INVENTION

The above-cited techniques are for imaging, using incoherent light (including a pulse signal). However, incoherent electromagnetic wave sources provide a lower output level and are less stable if compared with CW (continuous wave) electromagnetic wave sources to make it difficult to realize accurate measurements. Particularly, many incoherent electromagnetic wave sources in the terahertz wave region have problems including that the incoherent electromagnetic sources can produce only weak signals of the order of microwatts and require a large apparatus.

In view of the above-identified problems, the present invention provides a detection apparatus including a generating section for generating an incoherent electromagnetic wave, a first coupler section, a delaying section, a second coupler section, a detecting section and a signal processing section. The first coupler section splits the incoherent electromagnetic wave into a first wave and a second wave. The delay section delays the propagation time of the second wave by changing a propagation state thereof. The second coupler section couples the first wave whose propagation state was changed by a target of observation and the second wave whose propagation state was changed to produce a coupled wave having a correlation signal between the first and second waves. The detecting section detects the correlation signal of the coupled wave. The signal processing section acquires information on the target of observation based on a delay extent of the propagation time given by the delaying section and an intensity of the correlation signal detected by the detecting section. Additionally, the generating section includes an electromagnetic wave source for generating a coherent electromagnetic wave and a diffusing section for generating a pseudoincoherent electromagnetic wave by changing a propagation state of the coherent electromagnetic wave generated from the electromagnetic wave source by means of a code pattern that changes in time series.

In view of the above-identified problems, the present invention also provides an imaging apparatus for providing an internal image of the target of observation in the depth direction by means of the above detection apparatus, in which the signal processing section acquires information on an inside of the target of observation in the direction of propagation of the first wave based on a delay extent and an intensity of the correlation signal detected by the detecting section.

In a detection apparatus and an imaging apparatus according to the present invention, the intensity of the detection signal obtained by the detecting section is raised to allow observations to be made more accurately than ever because a coherent electromagnetic wave source can be employed with a relatively high output level. While theoretically an electromagnetic wave of any frequency can be used for the purpose of the present invention, the present invention is particularly remarkably advantageous for using a terahertz wave including frequencies within the frequency band between 30 GHz and 30 THz, for which it is difficult to provide a highly sensitive detector and a high power electromagnetic wave source.

Further features of the present invention will become apparent from the following description of exemplary embodiments with reference to the attached drawings.

BEST MODE FOR CARRYING OUT THE INVENTION

Now, the present invention will be described in greater detail by referring to the accompanying drawings. Throughout the drawings, the elements having the same feature are denoted by the same reference symbol.

Figure 1:
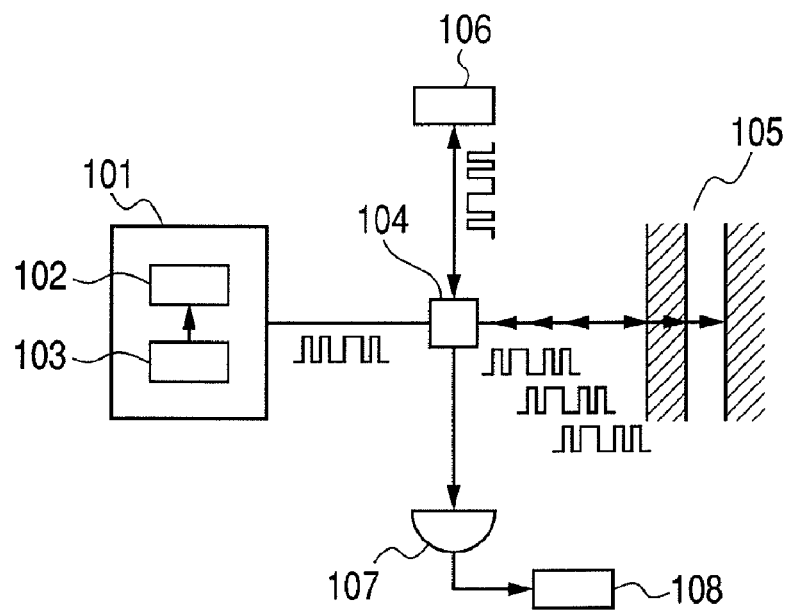
FIG. 1 is a schematic circuit diagram according to an embodiment of the present invention.

FIG. 1 is a schematic circuit diagram of an embodiment of imaging apparatus according to the present invention. Referring to FIG. 1, the imaging apparatus of this embodiment includes a generating section 101, a coupler section 104, a delaying section 106, a detecting section 107 and a signal processing section 108. The single coupler section 104 is provided with both the function of a first coupler section and that of a second coupler section. The function of the first coupler section is that of splitting the incoherent electromagnetic wave coming from the generating section 101. The function of the second coupler section is that of coupling the incoherent electromagnetic wave produced as a result of the split by the first coupler section and held in a propagation state changed by the sample (the target of observation) 105 and the incoherent electromagnetic wave held in a propagation state changed by the delaying section 106 and determines the correlation between them.

The generating section 101 includes a laser source 102 that is a coherent electromagnetic wave source and a diffusing section 103. The laser source 102 is a part that generates a coherent electromagnetic wave having a single wavelength (CW light). The diffusing section 103 operates to transform the coherent electromagnetic wave into a pseudoincoherent electromagnetic wave by temporally randomly modulating the electromagnetic wave generated from the laser source 102 (i.e. by pseudo-random modulation). More specifically, the diffusing section 103 transforms the coherent electromagnetic wave generated from the laser source 102 into a pseudoincoherent electromagnetic wave by way of digital ON/OFF intensity modulation, using an arbitrarily selected encoding signal that shows a code pattern, which changes in time series. The diffusing section 103 also generates a compression wave by way of analog modulation of the phase of the coherent electromagnetic wave as corresponding to the encoding signal and employs the compression wave as an incoherent electromagnetic wave. The diffusing section 103 may have any specific configuration so long as the diffusing section 103 can achieve the objective of generating a pseudoincoherent electromagnetic wave.

The coupler section 104 splits the incoherent electromagnetic wave output from the generating section 101 into an incoherent electromagnetic wave directed to the delaying section 106 and an incoherent electromagnetic wave directed to the sample 105 so as to make them show a predetermined ratio. Additionally, as pointed out above, the coupler section 104 couples the incoherent electromagnetic wave coming from the delaying section 106 and the incoherent electromagnetic wave coming from the sample 105 and outputs the coupled wave to the detecting section 107. The delaying section 106 delays the propagation time of the incoherent electromagnetic wave output to the delaying section 106 from the coupler section 104 by changing the propagation state thereof to provide a time delay.

The detecting section 107 operates to detect the intensity of the signal of the incoherent electromagnetic wave output from the coupler section 104. The signal processing section 108 monitors the detection signal of the detecting section 107 and the extent of the time delay produced by the delaying section 106 and computationally obtain information on the surface and the inside of the sample 105 in the depth direction thereof (the direction of propagation of electromagnetic wave). In this way, the signal processing section 108 acquires the internal profile of the sample 105 along the direction of propagation of the electromagnetic wave and, if necessary, displays an image of the inside of the object of observation on a display section.

Now, the operation of the embodiment will be described in greater detail by referring to the related drawings.

Referring to FIG. 1, the laser source 102 generates a coherent electromagnetic wave. The diffusing section 103 modulates the coherent electromagnetic wave by means of a predetermined code pattern to transform the coherent electromagnetic wave into an incoherent electromagnetic wave. In this embodiment, the diffusing section 103 digitally diffuses the output of the laser source 102 by means of ON-OFF switching. For the purpose of simplicity of explanation, assume that an 8-bit code pattern of (10001010) is employed for the diffusion.

The incoherent electromagnetic wave output from the generating section 101 arrives at the coupler section 104. The electromagnetic wave is then split into two incoherent electromagnetic waves, of which one is directed to the sample 105 and the other is directed to the delaying section 106. As illustrated in FIG. 1, the incoherent electromagnetic wave that gets to the sample 105 is reflected at the interfaces (indicated by the boundary lines of the hatched sections and the white sections) where the refractive index changes due to the substances at the opposite sides of the surface and in the inside. The reflected electromagnetic wave returns to the coupler section 104, where the electromagnetic wave is reflected again so as to be directed to the detecting section 107. The electromagnetic wave that gets to the coupler section 104 shows sequential time lags as a function of the number and the positions of the interfaces at the surface and in the inside of the sample 105 so that the electromagnetic wave appears like an echo signal.

On the other hand, the electromagnetic wave that gets to the delaying section 106 is reflected back to the coupler section 104 with a temporal delay that is provided by the delaying section 106.

Thus, both the electromagnetic wave reflected by the sample 105 and the electromagnetic wave reflected by the delaying section 106 arrive at the coupler section 104. The coupler section 104 makes the electromagnetic waves respectively reflected by and coming from the sample 105 and the delaying section 106 interfere with each other and outputs the electromagnetic wave produced as a result of the interference to the detecting section 107. The detecting section 107 detects the intensity of the interfered electromagnetic wave.

Figure 9A:
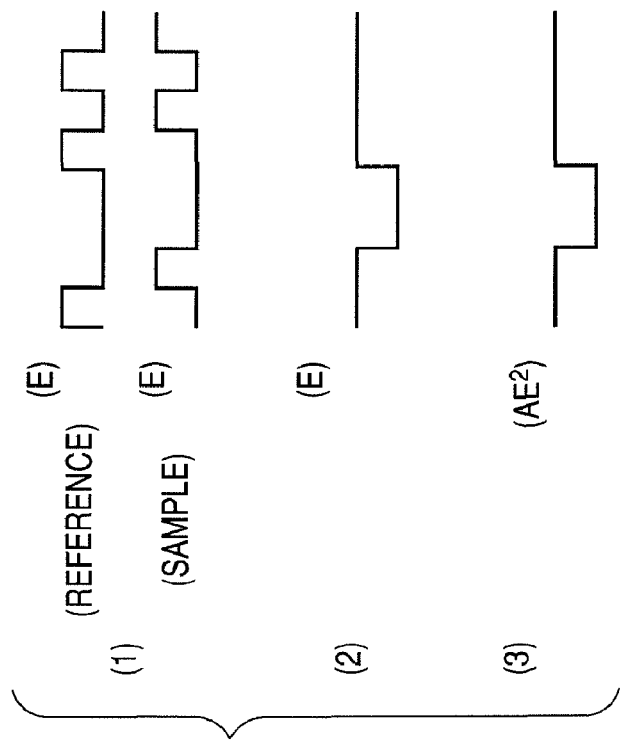
FIGS. 9A and 9B are schematic illustrations of the operation of an apparatus according to the present invention.
Figure 9B:
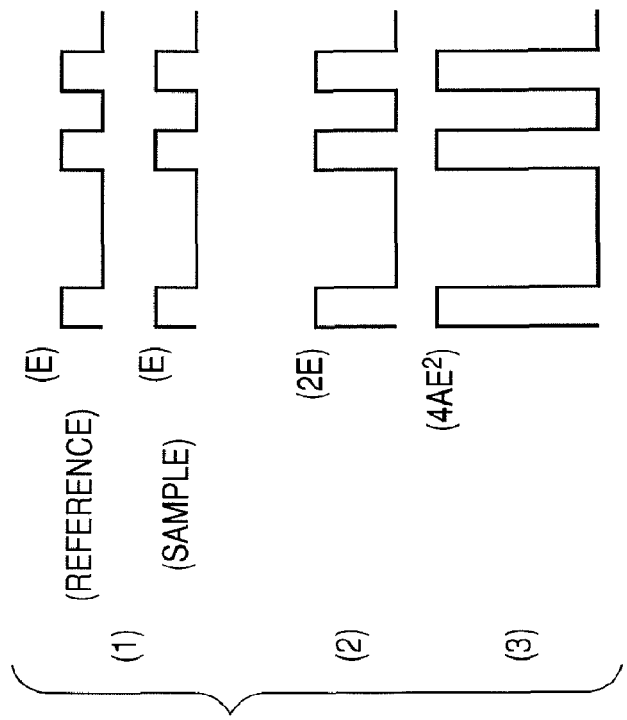

FIGS. 9A and 9B illustrate examples of signals. FIG. 9A illustrates the electromagnetic waves in time series reflected respectively by the sample 105 and the delaying section 106 that are fully correlated (i.e., arriving at the coupler section 104 at the same timing). On the other hand, FIG. 9B illustrates the electromagnetic waves in time series reflected respectively by the sample 105 and the delaying section 106 and arriving at the coupler section 104 with a time difference of 1-bit.

In FIGS. 9A and 9B, (1) shows the electric field amplitudes (E) of the electromagnetic waves input to the coupler section 104. More specifically, "(reference)" indicates the electromagnetic wave reflected by the delaying section 106 and arriving at the coupler section 104, whereas "(sample)" indicates the electromagnetic wave reflected by an interface of refractive index of the sample 105 and arriving at the coupler section 104. In FIGS. 9A and 9B, (2) illustrates the electric field amplitudes (E, 2E) of the electromagnetic wave produced as a result of interference of the two electromagnetic waves arriving at the coupler section 104 and output to the detecting section 107. As illustrated, the waveform of the electromagnetic wave output to the detecting section 107 varies depending on the timings at which the two electromagnetic waves arrive at the coupler section 104.

In FIGS. 9A and 9B, (3) illustrates the intensity signals of the electromagnetic wave that is detected by the detecting section 107. The detecting section 107 has a role of detecting the intensity signal of an electromagnetic wave and outputting a value that is proportional to the square of the electric field amplitude (E, 2E) of the electromagnetic wave that gets to the detecting section 107. The symbol A illustrated in FIGS. 9A and 9B represents a constant that is determined by the characteristics of the detecting section 107. While the signal waveforms shown in (3) are rectangular waveforms, waveforms where the high frequency component is attenuating (the waveform is declining) may be output depending on the time constant of the detecting section 107.

As illustrated in FIGS. 9A and 9B, the intensity waveform and the average intensity value of the electromagnetic wave detected by the detecting section 107 can vary depending on the timings at which the two original electromagnetic waves get to the coupler section 104. In other words, the mode of interference of the two electromagnetic waves varies depending on the timings at which they get to the coupler section 104. Thus, CW light emitted from the laser source 102 can be regarded as pseudo-incoherent light when the CW light is subjected to pseudo-random modulation at the diffusing section 103. Given that there is at present no way to generate incoherent electromagnetic wave sources of a high output level in the region of terahertz waves, an apparatus according to the present invention such as this embodiment can particularly advantageously be used for that region.

The signal processing section 108 determines the correlation of the signals arriving at the coupler section 104 on the basis of the output of the detecting section 107. More specifically, the signal processing section 108 determines that the two electromagnetic waves arriving at the coupler section 104 are fully correlated when the output of the detecting section 107 shows a desired waveform pattern (like the one illustrated in FIG. 9A) or when the detected average intensity value is maximized.

The imaging apparatus of this embodiment sweeps the delay produced at the delaying section 106 when detecting the series of flowing signals. Then, as a result, an interface of refractive index in the depth direction (the direction of propagation of electromagnetic wave in this instance) of the sample 105 can be identified and information on the sample 105 in the depth direction can be acquired on the basis of the delay produced at the delaying section 106 and the correlation detected by the detecting section 107. Then, three-dimensional information on the sample 105 can be obtained by conducting the above-described operation, while scanning the electromagnetic wave striking the sample 105 in an intraplanar direction (that is, in a direction perpendicular to the depth-direction). A moving mechanism for moving the sample 105 from above to below and vice versa in FIG. 1 or in opposite directions that are perpendicular to FIG. 1 may be used as a scanning unit for changing the relative positions of the electromagnetic wave being irradiated onto the object of observation 105 and the spot on the object of observation 105 that is being irradiated. Alternatively, a scanning system of moving the electromagnetic wave relative to the sample 105 by means of an optical system may be used. With such a scanning system, however, the optical system needs to be moved in such a way that the length of the propagation route from the coupler section 104 to the spot on the sample 105 where the electromagnetic wave being irradiated is always held constant. This is because, the correlation of the electromagnetic wave changes when the distance between the sample 105 and the coupler section 104 changes during the operation of scanning the electromagnetic wave. A distance gauging unit for gauging the distance between the coupler section 104 and the sample 105 may be provided separately to control the moving unit so as keep the distance equal to a constant value. Still alternatively, the results of the observation may be corrected by using the information on the distance between the coupler 104 and the sample 105.

The resolution in the depth direction is dependent on the state of signal diffusion of the diffusing section 103 of the generating section 101. In the case of the above-described arrangement, for instance, it depends on the time span in which the modulation using an 8-bit code pattern is effected. The resolution is about 0.3 mm when a coherent electromagnetic wave is diffused by means of an 8-bit encoding signal per 1 psec. The resolution is selected according to ability of the diffusing section 103 and the application of the imaging apparatus.

Figure 10:
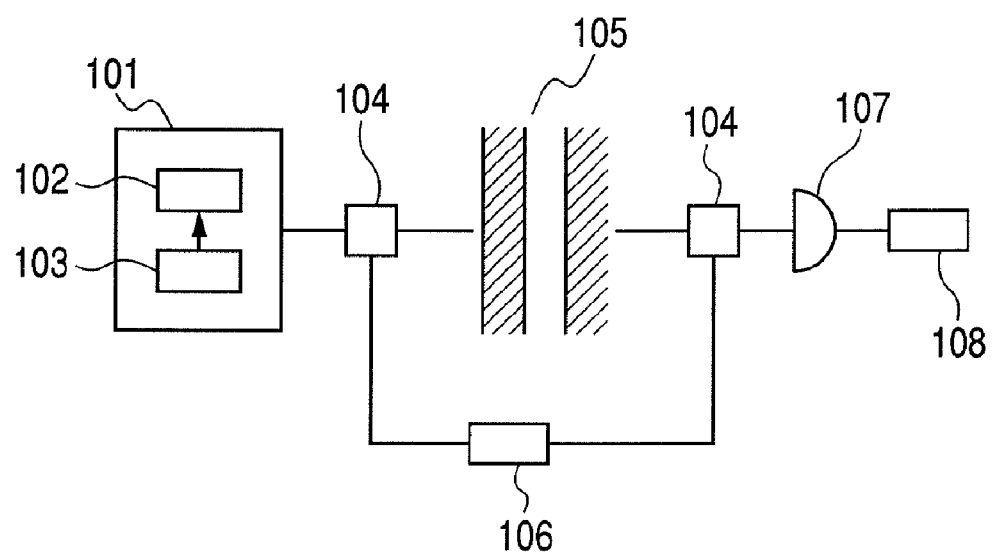
FIG. 10 is a schematic circuit diagram according to another embodiment of the present invention.

While a system adapted to use the electromagnetic waves reflected by the sample 105 and the delaying section 106 is described above, the present invention is by no means limited thereto. For example, a system adapted to use the electromagnetic waves transmitted through the sample 105 and the delaying section 106 may alternatively be formed as shown in FIG. 10. A first coupler section 104 and a second coupler section 104 are separately provided in the arrangement of FIG. 10.

This embodiment can also be so adapted as to operate as a detection apparatus for acquiring general information on the target of observation that is a substance having no internal profiles. For instance, it may be so arranged as to detect a signal indicating the presence of a target of observation and a signal indicating the absence of a target of observation as shown in FIG. 9A and determine the permittivity and the absorption coefficient of the target of observation by comparison. Then, the target of observation can be identified and some of the characteristics thereof may be examined on the basis of the obtained results. The permittivity and the absorption coefficient of the target of observation at a given depth can be detected.

The electromagnetic wave from the generating section 101 can be optically shaped to show a desired profile by means of one or more than one mirrors and/or one or more than one lenses. For example, the detecting operation can be conducted at high speed when the detecting section 107 is formed by an array of detectors in accordance with the shape of the linear electromagnetic waves.

The generating section 101 can be so arranged as to generate a plurality of incoherent electromagnetic waves. For example, a plurality of sets of generating sections 101 and detecting sections 107 may be arranged. The target of observation can be analyzed broadly in a short period of time with such an arrangement. The sets of generating sections 101 and detecting sections 107 may be so operated as to respectively analyze different regions of the target of observation or use different wavelength ranges and analyze the target of observation in the respective wavelength ranges. Alternatively, the sets of generating sections 101 and detecting sections 107 may be so operated as to observe the target of observation in the same wavelength range in order to analyze the target of observation more accurately by seeing the differences of the obtained signals. In a mode using a plurality of sets of generating sections 101 and detecting sections 107, the wavelengths and the code patterns respectively assigned them may be selected appropriately depending on the application. Crosstalks of each of the plurality of incoherent electromagnetic waves can be reduced by generating code patterns so as to make the electromagnetic waves show orthogonal relations.

When a plurality of sets of generating sections 101 and detecting sections 107 is provided, a broader image of the target of observation can be acquired within a short period of time by combining those sets with respective scanning units of the above-described type.

A compression wave may be used as incoherent electromagnetic wave for the purpose of the present invention. With this arrangement, the quantity of light of the electromagnetic wave that the detecting section 107 detects per unit is relatively increased if compared with the arrangement where the electromagnetic wave is digitally diffused by means of ON-OFF switching. Then, the extent to which the rate of change per unit time of the receivable diffusion signal is limited can be broadened. Thus, as a result, the detection sensitivity and hence the S/N are improved so that a high speed system can be realized.

Figure 7:
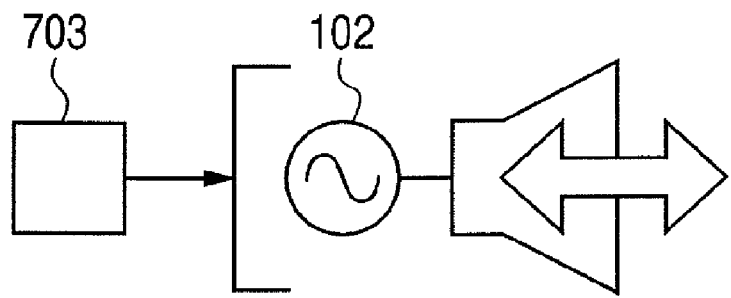
FIG. 7 is a schematic illustration of the operation of the diffusing section of Example 6 of the present invention.

When a compression wave is employed, a restoring section may be arranged on the route of electromagnetic wave between the coupler section 104 and the detecting section 107 to dissolve the compressed state of the compression wave. The restoring section may be configured in various different ways. More specifically, when an oscillation section 703, which is illustrated in FIG. 7 and will be described in greater detail hereinafter, is provided to oscillate the laser source 102 according to a code pattern to generate an incoherent electromagnetic wave, the detecting section 107 is also oscillated according to the same code pattern when the detecting section 107 receives the electromagnetic wave. When, for instance, a coarse part of the compression wave is arriving at the detecting section 107 as electromagnetic wave, the detecting section 107 is position-controlled so as to come closer to the coupler section 104. When, on the other hand, a dense part of the compression wave is arriving at the detection section 107, the latter is position-controlled so as to move away from the coupler section 104. The coarse/dense intervals of the electromagnetic wave can be made constant (an effect corresponding to restoration of a band) and the detecting section 107 can detect the electromagnetic wave with a restored band by conducting the position-control according to a code pattern.

Thus, with the above-described arrangement, pseudoincoherent light can be obtained from a CW electromagnetic wave source. Particularly, a compact electromagnetic wave source such as a single wavelength semiconductor laser that is less costly than any conventional incoherent electromagnetic wave sources can be used for the terahertz wave region to by turn downsize the entire apparatus and reduce the manufacturing cost of the apparatus. Additionally, a high output power coherent electromagnetic wave source can be used for an imaging apparatus and a detection apparatus according to the present invention. Then, the intensity of the signal detected by the detecting section is raised to allow more accurate observations. Then, information on a sample can be obtained in the depth direction from deeper positions in the sample.

EMBODIMENTS

Specific embodiments of the present invention will now be described below by referring to the related drawings. Note that the components of the embodiments of the present invention that have already described will not be described further hereinafter.

Embodiment 1

This embodiment relates to a possible configuration for realizing an imaging apparatus according to the present invention. In this embodiment, the present invention is applied to an imaging apparatus for acquiring information on a sample in the depth direction by means of a spatial optical system.

Figure 2:
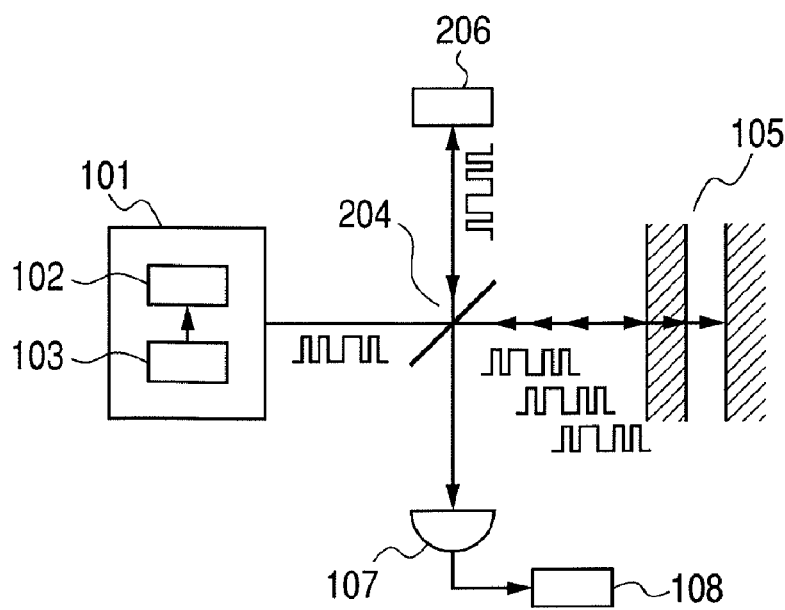
FIG. 2 is a schematic circuit diagram to be referred to for describing Example 1 of the present invention.

FIG. 2 is a schematic circuit diagram of the imaging apparatus of this embodiment. In this embodiment, a beam splitter 204 as shown in FIG. 2 is used as coupler section. A reflecting section 206 such as a mirror that optically reflects electromagnetic waves is used as delaying section.

A quantum cascade laser (QCL) is used for the laser source 102, although some other semiconductor device such as a resonant tunneling diode (RTD) may alternatively be used for the laser source 102. Still alternatively, an oscillator that utilizes a nonlinear optical crystal or an oscillator that utilizes an electron tube such as a backward wave oscillator (BWO) may be used for the laser source 102. While a laser source 102 is employed as electromagnetic wave source in this embodiment, an electromagnetic wave source of any other form may be used so long as it can radiate a single frequency component to the outside. Such an oscillator can be downsized with ease to emit a coherent electromagnetic wave with a relatively high output power level.

The diffusing section 103 of this embodiment is a driver for driving the laser source 102, which controls the laser output and operates for switching. An electro-thermic detector such as a bolometer is employed for the detecting section 107 of this embodiment. A detector of any form may be used for the detecting section 107 so long as the detector can detect the intensity of the electromagnetic wave that gets to the detector.

In this embodiment, the position of the reflecting section 206 is shifted in the direction of propagation of the electromagnetic wave. Information on the sample 105 in the depth direction thereof can be acquired by monitoring at the detecting section 107 the intensities of the plurality of electromagnetic waves that are made to interfere with each other by the beam splitter 204 and determining the correlation of the electromagnetic waves by means of the signal processing section 108.

With the above-described arrangement, an imaging apparatus in which the generating section 101 can be regarded as an incoherent electromagnetic wave source can be provided by using a CW electromagnetic wave source. Then, speckle noises that are peculiar to interference systems using a CW electromagnetic wave source can be reduced to improve the accuracy of observation.

Embodiment 2

This embodiment also relates to a possible configuration for realizing an imaging apparatus according to the present invention. More specifically, the imaging apparatus of this embodiment is obtained by modifying the apparatus of Embodiment 1 by using an optical waveguide for the electromagnetic wave propagation route.

Figure 3:
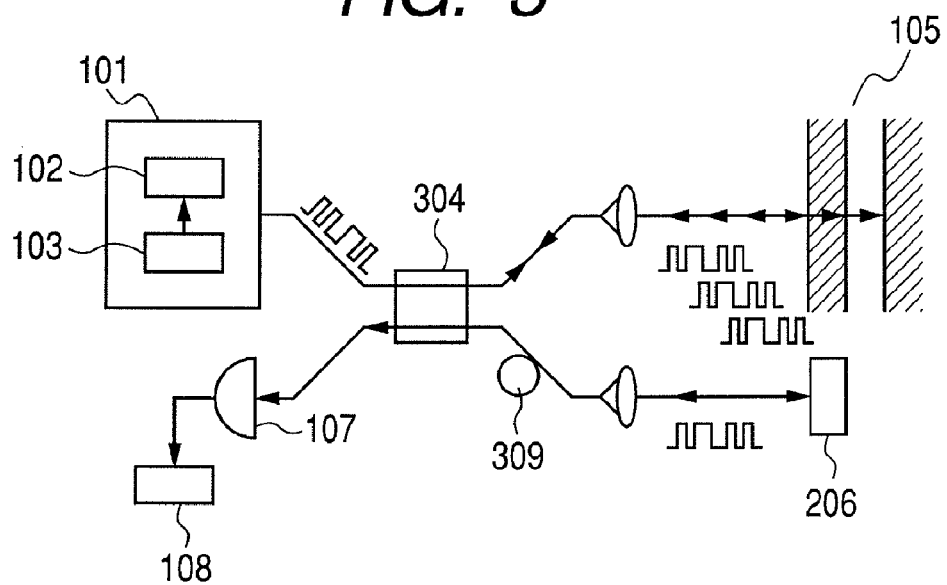
FIG. 3 is a schematic circuit diagram to be referred to for describing Example 2 of the present invention.

FIG. 3 is a schematic circuit diagram of the imaging apparatus of this embodiment. As shown in FIG. 3, an optical waveguide 309 of optical fiber is employed for the electromagnetic wave propagation route. A fiber coupler 304 is employed for the coupler section 104 correspondingly.

With this arrangement, the optical waveguide 309 operates as main electromagnetic wave propagation route. As a result, any possible interferences between the electromagnetic wave and external noises can be reduced to improve the S/N ratio and hence the accuracy of observation. Additionally, this arrangement of using an optical waveguide 309 of optical fiber can simplify the optical axis adjusting operation to provide an advantage of ease handling if compared with a spatial optical system. Furthermore, this arrangement of using an optical waveguide 309 of optical fiber can improve the degree of freedom of installation. Otherwise, this embodiment provides advantages similar to those of Embodiment 1.

Embodiment 3

This embodiment differs from the above-described embodiments in terms of the method of generating a pseudoincoherent electromagnetic wave by means of the generating section 101. More specifically, an incoherent electromagnetic wave is produced by mechanically sequentially switching the part that transmits an electromagnetic wave and the part that reflects an electromagnetic wave according to a code pattern that changes in time series as described earlier.

Figure 4:
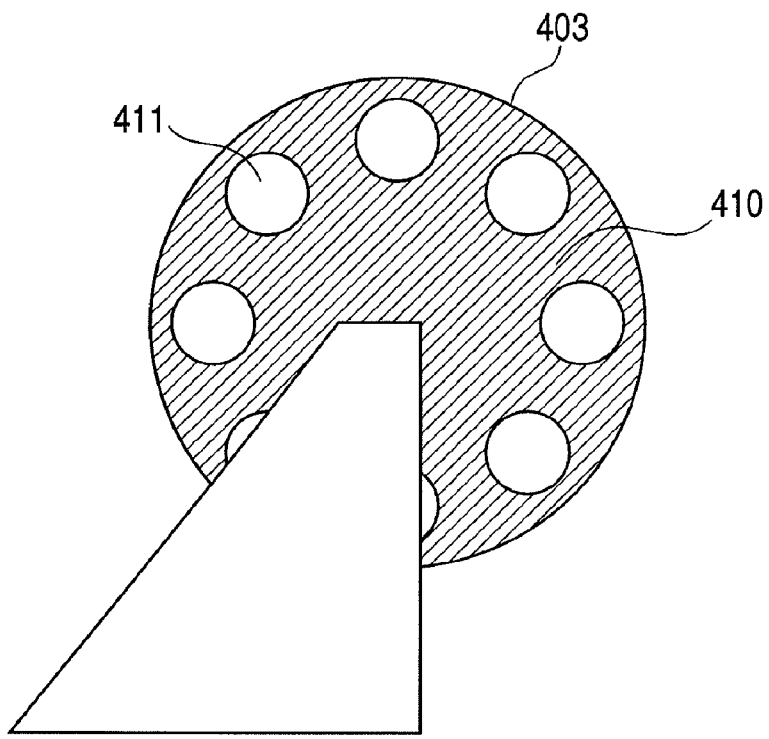
FIG. 4 is a schematic illustration of the rotary disk that is used as diffusing section in Example 3 of the present invention.

For example, a rotary disk 403 as shown FIG. 4 is employed for the diffusing section 103. Referring to FIG. 4, the rotary disk 403 has reflecting sections 410 that reflect an electromagnetic wave and transmitting sections 411 that transmit an electromagnetic wave. The reflecting sections 410 are typically made of an electro-conductive metal. The transmitting sections 411 may be cavities that may or may not be filled with a substance that is maximally transparent relative to the electromagnetic wave to be transmitted through them. The rotary disk 403 is driven to rotate around the axis of rotation that extends in the normal direction relative to FIG. 4.

An electromagnetic wave strikes the rotary disk 403 in a direction that substantially runs in parallel with the axis of rotation. The electromagnetic wave that strikes the rotary disk 403 is turned into a pseudoincoherent electromagnetic wave as the electromagnetic wave alternately encounters the reflecting sections 410 and the transmitting sections 411 that are successively switched on the propagation route of the electromagnetic wave.

While the reflecting sections 410 and the transmitting sections 411 are arranged regularly in FIG. 4, they are actually arranged according to the code pattern for generating an incoherent electromagnetic wave. Thus, reflecting sections 410 and transmitting sections 411 are arranged according to the code pattern. Alternatively, an electromagnetic wave can be turned into an incoherent electromagnetic wave by changing the number of revolutions per unit time of the rotary disk 403 according to the code pattern. Then, it is not necessary to select the number of reflecting sections 410, that of transmitting sections 411 and the pitch of arrangement of those sections according to the code pattern.

A reflectionless coat may be applied to the rotary disk 403 or an SWS (sub wavelength structure) may be formed in the rotary disk 403 in order to make the rotary disk 403 partly free from reflection. While a rotary drive system is employed in this embodiment to generate an incoherent electromagnetic wave, a linear drive system for translating a diffusing member having reflecting sections and transmitting sections may alternatively be used in this embodiment.

This embodiment provides an advantage that an imaging apparatus can be prepared with ease and operate stably because an incoherent electromagnetic wave is produced mechanically. Otherwise, this embodiment provides advantages similar to those of the preceding embodiments.

Embodiment 4

This embodiment differs from the preceding embodiments in terms of the method of generating a pseudoincoherent electromagnetic wave by means of the generating section 101. More specifically, an incoherent electromagnetic wave is produced by changing the propagation rate of the coherent electromagnetic wave according to a code pattern.

Figure 5:
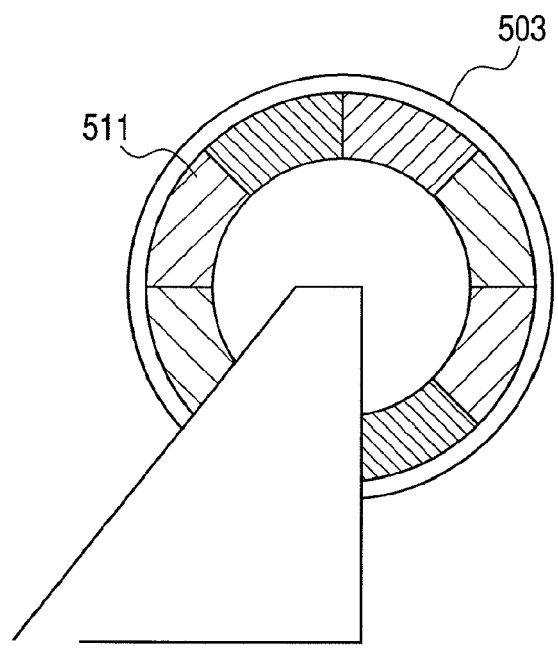
FIG. 5 is a schematic illustration of the rotary disk that is used as diffusing section in Example 4 of the present invention.

A rotary disk 503 as illustrated in FIG. 5 is used for the diffusing section 103 of this embodiment. The rotary disk 503 has a plurality of transmitting sections 511 providing different propagation rates for an electromagnetic wave as illustrated in FIG. 5. For example, the delay times of the plurality of transmitting sections 511 are controlled and differentiated by selecting different thicknesses for them. While a quartz substrate is employed for the transmitting sections of this embodiment, the substance of the transmitting sections 511 is by no means limited thereto so long as the substance can achieve the objective of the transmitting sections 511. Alternatively, different substances may be used to form the transmitting sections 511 in order to control the propagation state of the electromagnetic wave being transmitted through the rotary disk 503. The substance that is used to form the transmitting sections 511 is preferably maximally transparent relative to the electromagnetic wave being transmitted. As in the case of Embodiment 3, the rotary disk 503 is driven to rotate around the axis of rotation that extends in the normal direction relative to FIG. 5. An electromagnetic wave strikes the rotary disk 503 in a direction that substantially runs in parallel with the axis of rotation.

The phase of the electromagnetic wave that strikes the rotary disk 503 is shifted on the propagation route thereof by the plurality of transmitting sections 511 that are switched successively so that the electromagnetic wave is propagated further as a compression wave showing a waveform according to the code pattern. The compression wave operates as a pseudoincoherent electromagnetic wave.

While the plurality of transmitting sections 511 is arranged regularly in FIG. 5, the areas occupied respectively by the transmitting sections 511 are actually differentiated according to the code pattern for generating an incoherent electromagnetic wave. Alternatively, an incoherent electromagnetic wave can be produced by changing the revolutions per unit time of the rotary disk 503 according to the code pattern. Then, the number of the plurality of transmitting sections 511 may not necessarily be dependent on the code pattern.

A compression wave showing a waveform according to a code pattern is employed as pseudoincoherent electromagnetic wave in this embodiment. The average power per unit time of such a compression wave can be made high if compared with an incoherent electromagnetic wave produced by means of switching operation in order to maintain a state where an electromagnetic wave is generated constantly. In other words, the efficiency of utilizing an electromagnetic wave is improved to allow more accurate observations. Then, information on a sample can be obtained in the depth direction from deeper positions in the sample. Otherwise, this embodiment provides advantages similar to those of Embodiment 3.

Embodiment 5

This embodiment differs from the preceding embodiments in terms of the method of generating a pseudoincoherent electromagnetic wave by means of the generating section 101. More specifically, an incoherent electromagnetic wave is produced by changing the propagation state of an electromagnetic wave according to a code pattern by means of a MEMS (micro electro mechanical systems) technique.

Figure 6:
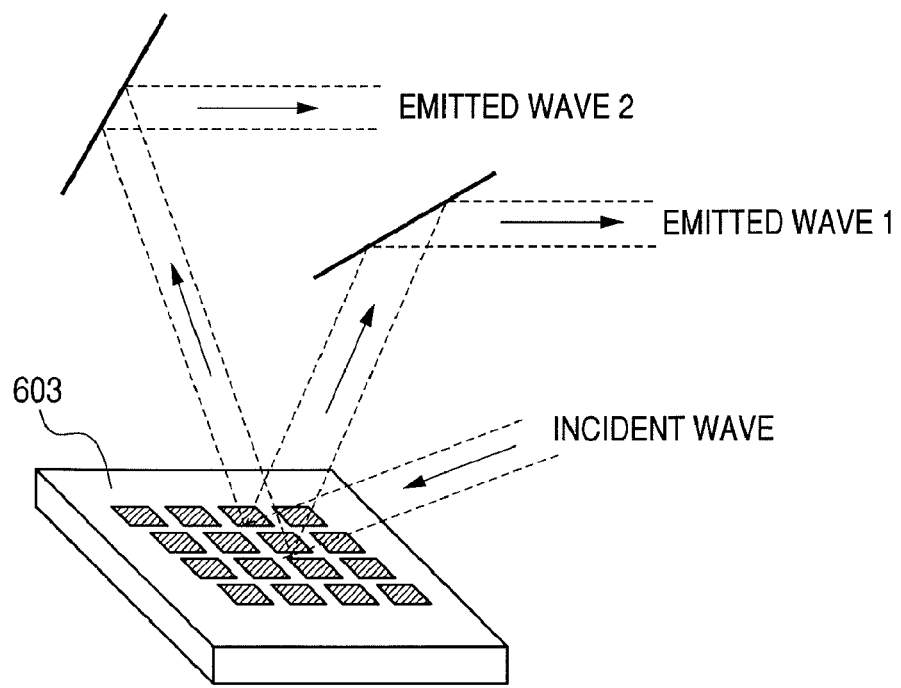
FIG. 6 is a schematic illustration of the micro mirror that is used as diffusing section in Example 5 of the present invention.

In this embodiment, a MEMS device formed by integrally arranging micro mirrors as shown in FIG. 6 is employed for the diffusing section 103. The MEMS device of FIG. 6 has a plurality of switching sections 603 that are movable micro mirrors and the propagation delay time of the emitted wave is controlled for the time when the wave gets to the coupler section 104 by shifting the direction of reflection of the incident electromagnetic wave. As a result, a compression wave showing a waveform according to a code pattern is produced. While two electromagnetic wave propagation routes (emitted wave 1, emitted wave 2) are shown in FIG. 6, there may be three or more than three electromagnetic wave propagation routes. An emitted wave can be switched on and off according to the code pattern on an electromagnetic wave propagation route to produce an incoherent electromagnetic wave. The switching sections 603 are typically driven to swing by an electromagnetic drive unit having magnets and coils or an electrostatic force drive unit having oppositely disposed electrodes.

While micro mirrors are used for the diffusing section 103 of this embodiment, other devices realized by using a MEMS technique (e.g., switching devices) may alternatively be used for the embodiment. When fiber type waveguides as shown in FIG. 3 are employed, a similar operation can be realized by selecting a fiber waveguide for introducing an electromagnetic wave out of a plurality of fiber waveguides showing different propagation states by means of MEMS switches according to the code pattern.

The propagation state of the electromagnetic wave is controlled according to the code pattern by means of devices formed by applying a MEMS technique in order to produce an incoherent electromagnetic wave in this embodiment. Then, as a result, the entire apparatus can be downsized with ease. Additionally, since the devices are small, the mechanical resonance frequency rises so that the operation of modulation according to the code pattern can be conducted at high speed. Then, as a result, information on the sample 105 can be obtained in the depth direction with a higher resolution. Otherwise, this embodiment provides advantages similar to those of the preceding embodiments.

Embodiment 6

This embodiment differs from the preceding embodiments in terms of the method of generating a pseudoincoherent electromagnetic wave by means of the generating section 101. More specifically, the propagation state of an electromagnetic wave is controlled by oscillating the electromagnetic wave source 102 in the direction of propagation of the electromagnetic wave according to a code pattern.

In this embodiment, the laser source 102 is rigidly anchored to an oscillating section 703 that is an actuator as shown in FIG. 7 and driven to oscillate in the direction of propagation of the electromagnetic wave. As a result, the propagation delay time of the electromagnetic wave can be controlled for the time when the electromagnetic wave gets to the coupler section 104 to form a compression wave showing a waveform according to the code pattern. The moving distance of the laser source 102 given by the oscillating section 703 is preferably between $\pi$ and $-\pi$ when reduced to phase.

Thus, this embodiment can produce an incoherent electromagnetic wave by means of a simple arrangement of oscillating the laser source 102. Particularly, since no control device is inserted into the propagation route of electromagnetic wave for the purpose of changing the propagation state of electromagnetic wave, the loss that can be caused by such a device is nil. Then, the target of observation can be observed more accurately and information on the target of observation can be obtained with ease from deeper positions thereof. Otherwise, this embodiment provides advantages similar to those of the preceding embodiments.

Embodiment 7

This embodiment differs from the preceding embodiments in terms of the method of generating a pseudoincoherent electromagnetic wave by means of the generating section 101. More specifically, the propagation state of an electromagnetic wave is controlled by mechanically changing the length of the propagation route of electromagnetic wave according to a code pattern.

Figure 8:
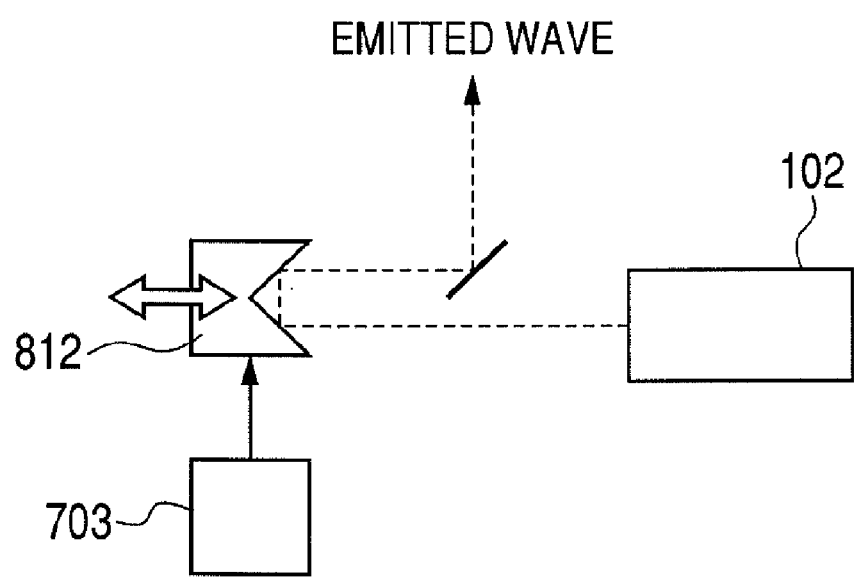
FIG. 8 is a schematic illustration of the operation of the diffusing section of Example 7 of the present invention.

In this embodiment, a delay optical section 812 is rigidly anchored to an oscillating section 703 that is an actuator as shown in FIG. 8 and driven to oscillate to change the length of the optical path of electromagnetic wave. Then, as a result, the state of the propagation delay of the electromagnetic wave getting to the coupler section 104 can be controlled to produce a compression wave showing a waveform according to the code pattern. In this embodiment again, the moving distance of the delay optical section 812 given by the oscillating section 703 is preferably between $\pi$ and $-\pi$ when reduced to phase.

When a fiber type waveguide as shown in FIG. 3 is employed, a similar motion can be produced by expanding and contracting the waveguide. For example, the waveguide can be mechanically expanded and contracted by means of an actuator arranged outside the fiber.

An incoherent electromagnetic wave is produced by oscillating an optical device that controls the propagation state of electromagnetic wave in this embodiment. Since the device is very small and lightweight, the mechanical resonance frequency rises so that the operation of modulation according to the code pattern can be conducted at high speed. Then, as a result, information on the sample 105 can be obtained in the depth direction with a higher resolution. Otherwise, this embodiment provides advantages similar to those of the preceding embodiments.

Embodiment 8

This embodiment differs from the preceding embodiments in terms of the method of generating a pseudoincoherent electromagnetic wave by means of the generating section 101. More specifically, the propagation state of electromagnetic wave is controlled according to a code pattern by means of external energy.

For example, an electro-optic device whose refractive index can be changed by externally applying an electric field thereto is arranged on the propagation route of electromagnetic wave. The electro-optic device may be made of a substance such as BBO crystal, $LiTzO_3$ crystal, KTP crystal or ZnTe crystal whose refractive index can be changed by externally applying an electric field. When a fiber type waveguide as shown in FIG. 3 is employed, the fiber type waveguide may be so arranged that the refractive index of the clad material of the fiber is changed by externally applying an electric field.

Thus, the length of the optical path of electromagnetic wave is changed by means of a device for controlling the propagation of an electromagnetic wave by means of an external electric field in this embodiment. Then, as a result, the state of the propagation delay of the electromagnetic wave getting to the coupler section 104 can be controlled to produce a compression wave showing a waveform according to the code pattern.

Thus, the propagation state of an electromagnetic wave is controlled by means of external energy typically by applying an electric field in this embodiment. Then, as a result, the operation of modulation can be conducted at high speed. Thus, this embodiment provides an advantage that information on the sample 105 can be obtained in the depth direction with a higher resolution.

Embodiment 9

This embodiment relates to a possible configuration for realizing an imaging apparatus according to the present invention. More specifically, this embodiment relates to multiplexing. With this embodiment, information on a sample 105 is acquired in the depth direction thereof by means of a plurality of incoherent electromagnetic waves that are modulated by a plurality of code patterns. Preferably, the code patterns show orthogonal relations.

With this embodiment, information on a sample 105 is acquired by irradiating a sample 105 with a plurality of electromagnetic waves. Then, the imaging operation can be conducted with ease at high speed. Particularly, crosstalks of the electromagnetic waves can be reduced to maintain a high degree of accuracy of observation by modulating the electromagnetic waves by means of code patterns showing orthogonal relations.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2007-092831, filed on Mar. 30, 2007, which is hereby incorporated by reference herein in its entirety.

The invention claimed is:

1. A detection apparatus comprising:
a generating section for generating an incoherent electromagnetic wave, wherein the incoherent electromagnetic wave is a compression wave;
a first coupler section for splitting the incoherent electromagnetic wave into a first wave and a second wave;
a delaying section for delaying a propagation time of the second wave by changing a propagation state thereof;
a second coupler section for coupling the first wave, whose propagation state has been changed by a target of observation, and the second wave, whose propagation state has been changed by said delaying section, to produce a coupled wave having a correlation signal between the first and the second waves;
a detecting section for detecting the correlation signal of the coupled wave;
a signal processing section for acquiring information on the target of observation based on a delay extent of the propagation time given by said delaying section and an intensity of the correlation signal detected by said detecting section; and
a restoring section for dissolving coarse and dense states of the compression wave on a propagation route of electromagnetic wave arranged between said second coupler section and said detecting section,
wherein said generating section includes an electromagnetic wave source for generating a coherent electromagnetic wave and a diffusing section for generating the pseudo-incoherent electromagnetic wave by changing a propagation state of the coherent electromagnetic wave generated by said electromagnetic wave source in accordance with a code pattern that changes in time series.

2. The apparatus according to claim 1, wherein a single coupler section operates as both said first coupler section and said second coupler section.

3. The apparatus according to claim 1, wherein said generating section generates a plurality of incoherent electromagnetic waves.

4. The apparatus according to claim 3, wherein the plurality of incoherent electromagnetic waves have orthogonal relations.

5. The apparatus according to claim 1, further comprising a scanning unit for changing relative positions between the first wave and the target of observation to be irradiated with the first wave.

6. The apparatus according to claim 1, wherein the incoherent electromagnetic wave includes frequencies within a frequency band between 30 GHz and 30 THz.

7. The apparatus according to claim 1, wherein said signal processing section provides an inner image of the target of observation in the depth direction by acquiring information on an inside of the target of observation in the direction of propagation of the first wave based on a delay extent of the propagation time given by said delaying section and an intensity of the correlation signal detected by said detecting section.

8. The apparatus according to claim 1, wherein the first and the second waves include frequencies within a frequency band between 30 GHz and 30 THz.

9. A detection apparatus comprising:
a generating section for generating an incoherent electromagnetic wave, wherein the incoherent electromagnetic wave is a compression wave;
a first coupler section for splitting the incoherent electromagnetic wave which comes from said generating section into a first wave and a second wave;
a delaying section for delaying a propagation time of the second wave by changing a propagation state thereof;
a second coupler section for coupling the first wave, whose propagation state has been changed by a target of observation, and the second wave, whose propagation state has been changed by said delaying section, to produce a coupled wave having a correlation signal between the first and the second waves;
a detecting section for detecting the correlation signal of the coupled wave;
a signal processing section for acquiring information on the target of observation based on a delay extent of the propagation time given by said delaying section and an intensity of the correlation signal detected by said detecting section; and
a restoring section for dissolving coarse and dense states of the compression wave on a propagation route of electromagnetic wave arranged between said second coupler section and said detecting section,
wherein said generating section includes an electromagnetic wave source for generating a coherent electromagnetic wave and a diffusing section for generating the pseudo-incoherent electromagnetic wave as corresponding to an encoding signal in time series by changing a propagation state of the coherent electromagnetic wave generated by said electromagnetic wave source in accordance with a code pattern that changes in time series.

10. The apparatus according to claim 9, wherein the first and the second waves include frequencies within a frequency band between 30 GHz and 30 THz.

* * * * *